US008818063B2

(12) United States Patent
Suehira

(10) Patent No.: US 8,818,063 B2
(45) Date of Patent: Aug. 26, 2014

(54) OPTICAL COHERENCE TOMOGRAPHY METHOD AND OPTICAL COHERENCE TOMOGRAPHY APPARATUS

(75) Inventor: Nobuhito Suehira, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 932 days.

(21) Appl. No.: 12/709,033

(22) Filed: Feb. 19, 2010

(65) Prior Publication Data
US 2010/0226553 A1 Sep. 9, 2010

(30) Foreign Application Priority Data
Mar. 6, 2009 (JP) ................................. 2009-053793

(51) Int. Cl.
| G06K 9/00 | (2006.01) |
| G01B 9/02 | (2006.01) |
| A61B 5/00 | (2006.01) |
| G01N 21/47 | (2006.01) |
| A61B 3/10 | (2006.01) |

(52) U.S. Cl.
CPC ........ *G01B 9/02044* (2013.01); *G01B 9/02085* (2013.01); *G01B 9/02078* (2013.01); *A61B 5/0073* (2013.01); *G01B 9/02091* (2013.01); *G01B 9/02063* (2013.01); *A61B 5/0066* (2013.01); *G01N 21/4795* (2013.01); *A61B 3/102* (2013.01)
USPC ........................................................ 382/131

(58) Field of Classification Search
CPC .................... G06T 2207/10101; A61B 3/102; A61B 5/006
USPC ........................................................ 382/131
See application file for complete search history.

(56) References Cited

U.S. PATENT DOCUMENTS

| 6,377,349 | B1 | 4/2002 | Fercher |
| 7,248,907 | B2 | 7/2007 | Hogan |
| 7,364,296 | B2 * | 4/2008 | Miller et al. .................. 351/206 |
| 7,527,378 | B2 | 5/2009 | Fukuma et al. |

(Continued)

FOREIGN PATENT DOCUMENTS

| DE | 11-2006-003-228 T5 | 10/2008 |
| EP | 2251637 A1 | 11/2010 |

(Continued)

OTHER PUBLICATIONS

Donald T. Miller ; Junle Qu ; Ravi S. Jonnal ; Karen E. Thorn; Coherence gating and adaptive optics in the eye. Proc. SPIE 4956, Coherence Domain Optical Methods and Optical Coherence Tomography in Biomedicine VII, 65 (Jul. 1, 2003); doi:10.1117/12.477633.*

(Continued)

*Primary Examiner* — John Pauls
*Assistant Examiner* — Jonathan Durant
(74) *Attorney, Agent, or Firm* — Fitzpatrick, Cella, Harper & Scinto

(57) ABSTRACT

An optical coherence tomography method according to the present invention comprises the steps of dividing an object to be measured into a plurality of measurement regions adjacent to one another in a direction of irradiation of a measurement light, and acquiring a measurement image for every measurement region based on a wavelength spectrum of a coherent light; correcting, for every measurement region, a contrast of the measurement image of the measurement region; and acquiring, for every measurement region, a tomographic image from the corrected measurement image.

27 Claims, 7 Drawing Sheets

(56) References Cited

U.S. PATENT DOCUMENTS

| | | | |
|---|---|---|---|
| 7,823,782 B2 | 11/2010 | Yatagai et al. | |
| 8,199,327 B2 * | 6/2012 | Nebosis et al. | 356/479 |
| 8,200,306 B2 | 6/2012 | Hogan et al. | |
| 8,204,300 B2 | 6/2012 | Sugita et al. | |
| 8,330,962 B2 * | 12/2012 | Nebosis et al. | 356/479 |
| 8,339,610 B2 * | 12/2012 | Nebosis et al. | 356/479 |
| 8,390,819 B2 | 3/2013 | Suehira | |
| 2006/0089548 A1 | 4/2006 | Hogan | |
| 2007/0002327 A1 * | 1/2007 | Zhou et al. | 356/456 |
| 2007/0188704 A1 | 8/2007 | Fukuma et al. | |
| 2007/0260128 A1 | 11/2007 | Hogan et al. | |
| 2009/0079993 A1 | 3/2009 | Yatagai et al. | |
| 2010/0166293 A1 | 7/2010 | Sugita et al. | |
| 2012/0218557 A1 | 8/2012 | Sugita et al. | |

FOREIGN PATENT DOCUMENTS

| | | |
|---|---|---|
| JP | 11-325849 | 11/1999 |
| JP | 2006-201087 A | 8/2006 |
| JP | 2007-215733 A | 8/2007 |
| JP | 2008-517664 A | 5/2008 |
| JP | 2008-253493 A | 10/2008 |
| JP | 2008-275529 A | 11/2008 |
| JP | 2008-298767 A | 12/2008 |
| WO | 2007/060973 A1 | 5/2007 |

OTHER PUBLICATIONS

Jan. 18, 2013 European Communication in European Patent Appln. No. 10152650.7.

Yimin Wang, et al., Ultrahigh-resolution optical coherence tomography by broadband continuum generation from a photonic crystal fiber, Optics Letters, vol. 28, No. 3, Feb. 1, 2003, pp. 182-184.

Notification of the First Office Action dated Apr. 25, 2011, in counterpart Chinese Application No. 201010123799.5.

Communication dated Oct. 15, 2010 and European Search Report, ("ESR") in counterpart European Application No. 10152650.7-2213.

Dirk J. Faber, Freek J. Van Der Meer, and Maurice C.G. Aalders, Quantitative measurement of attenuation coefficients of weakly scattering media using optical coherence tomography, Optics Express, vol. 12, No. 19, Sep. 20, 2004, pp. 4353-4365.

Jon Holmes, Simon Hattersley, Nick Stone, Florian Bazant-Hegemark, and Hugh Barr, Multi-channel Fourier domain OCT system with superior lateral resolution for biomedical applications, Proc. of SPIE, vol. 6847, Feb. 18, 2008, pp. 684700-1-684700-9.

* cited by examiner

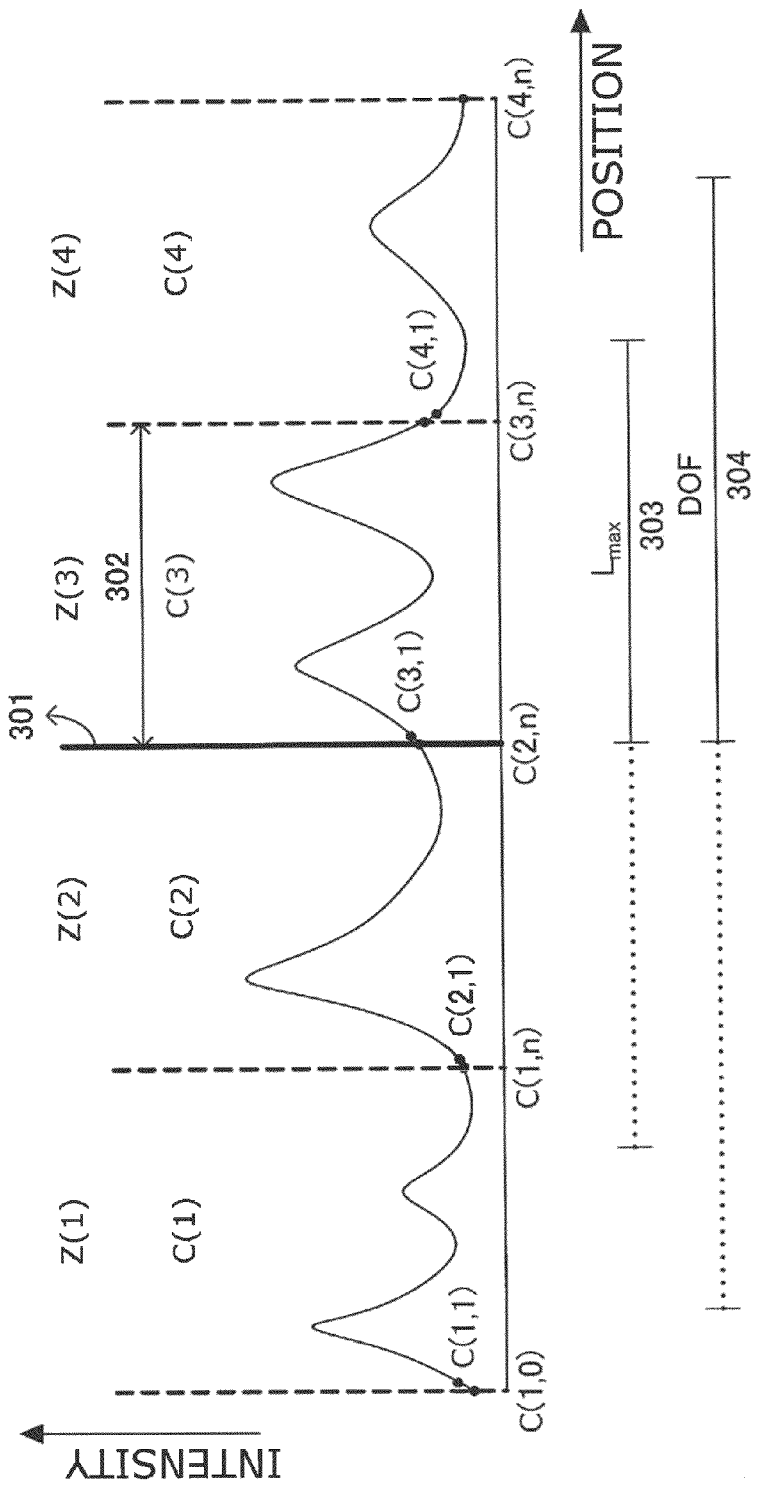

OPTICAL COHERENCE TOMOGRAPHY METHOD AND OPTICAL COHERENCE TOMOGRAPHY APPARATUS

BACKGROUND OF THE INVENTION

1. Field of the Invention

The present invention relates to an optical coherence tomography method and an optical coherence tomography apparatus, and more particularly to an optical coherence tomography method and an optical coherence tomography apparatus, using a coherent optical system for use in the medical field.

2. Description of the Related Art

Currently, there are a wide variety of ophthalmic devices using optical devices. Examples of such ophthalmic devices include anterior eye imaging apparatuses, retinal cameras and scanning laser ophthalmoscopes (SLOs). Among them, optical coherence tomography (OCT) apparatuses can obtain tomographic images of objects to be measured at high resolution, and therefore are becoming indispensable devices for outpatient medical treatments specialized for retinas.

An OCT apparatus is disclosed, for example, in Japanese Patent Application Laid-Open No. H11-325849. In an OCT apparatus disclosed in Japanese Patent Application Laid-Open No. H11-325849, low coherent light is used. Light from a light source is divided into measurement light and reference light through a split optical path, such as a beam splitter. The measurement light is applied onto an object to be measured, such as a human eye, through a measurement optical path, and return light from the object to be measured is led to a detection position through a detection optical path. The return light as used herein refers to reflected light or scattered light that includes information on an interface of the object to be measured with respect to the irradiation direction of light. The reference light is led to a detection position through a reference optical path. Input to a detection position is coherent light resulting from interference between the return light and the reference light. Then, the wavelength spectrum of the coherent light is collectively acquired by the use of a spectrometer or the like, and the wavelength spectrum is Fourier transformed, thereby obtaining a tomographic image of the object to be measured. In general, an OCT apparatus that collectively measures the wavelength spectrum is termed a spectral-domain OCT (SD-OCT) apparatus.

With an SD-OCT apparatus, the depth of focus and a transversal resolution can be adjusted by selecting a numerical aperture (NA) of a lens used for controlling a focusing position of the measurement light in an object to be measured. For example, the larger the numerical aperture, the smaller the depth of focus, but the higher the transversal resolution. On the other hand, if the numerical aperture is reduced, the depth of focus becomes larger, but the transversal resolution becomes lower. In other words, the relationship between the depth of focus and the transversal resolution is a trade-off.

As a method that overcomes the problems with this relationship, dynamic focus OCT is disclosed in "OPTICS LETTERS Vol. 28, 2003, pp. 182-184". In this mode, time domain OCT (TD-OCT) that acquires a tomographic image while changing an optical path length is employed. Then, a tomographic image is acquired while changing the optical path length and moving the focus position of a lens in synchronization with each other. As a result, while the transversal resolution is maintained high, the measurement range of an object to be measured (the range in the irradiation direction of measurement light in an acquired tomographic image) can be increased.

SUMMARY OF THE INVENTION

In TD-OCT, however, measurement is performed while, consecutively changing the optical path length. Therefore, it takes more time to acquire (measure) a tomographic image with TD-OCT than with SD-OCT. In order to achieve high-speed acquisition of a tomographic image having a large measurement range of an object to be measured and a high transversal resolution, a method of performing dynamic focusing in a spectral-domain mode is considered. As described above, in the spectral-domain mode, as the transversal resolution increases, the depth of focus decreases. Accordingly, to increase the measurement range, an object to be measured needs to be divided into a plurality of measurement regions adjacent to one another along the irradiation direction of measurement light for the purpose of measurement.

In SD-OCT, a phenomenon as illustrated in FIG. 7 occurs. FIG. 7 illustrates a relationship of a distance between a coherence gate and a mirror on a horizontal axis and a measured intensity on a for vertical axis (intensity of light; reflected intensity) in the case of using the mirror as an object to be measured. Specifically, intensities (digital values) measured when the position of the mirror is distant from the coherence gate by 50, 100, 150, 200, 300, 400, 500, 600, 800, 1000, 1200, 1600 and 2000 μm are shown. Note that the term "coherence gate" refers to a position that is in the measurement optical path and that has the same optical distance as that of the reference optical path. The dotted line schematically shows the envelop of their results (changes in intensity with respect to the position in the irradiation direction in the measurement region), which is a so-called attenuation function. In FIG. 7, as the position of the mirror is more distant from the coherence gate, the intensity attenuates more. This is called "roll-off" or the like, and occurs because of the resolution of a spectrometer and so on.

As described above, in the case of this the phenomenon occurring, the intensity is stronger as the position is closer to the coherence gate, whereas the intensity is weaker as the position is more distant from the coherence gate. Therefore, at a boundary of measurement regions, the intensity is strong in one region whereas the intensity is weak in the other region. This causes a jump in the measured intensity between regions adjacent to each other.

Accordingly, an object of the invention is to provide an optical coherence tomography method and an optical coherence tomography apparatus, that can continuously join a tomographic image acquired from each of a plurality of measurement regions.

An optical coherence tomography method divides light from a light source into measurement light and reference light and acquires a tomographic image of an object to be measured on a basis of a wavelength spectrum of coherent light of the reference light and return light, the return light returning from the object to be measured upon applying the measurement light onto the object to be measured. The optical coherence tomography method also comprises the steps of:

dividing the object to be measured into a plurality of measurement regions adjacent to one another in a direction of irradiation of the measurement light, and acquiring a measurement image for every measurement region based on the wavelength spectrum of the coherent light;

correcting, for every measurement region, a contrast of the measurement image of the measurement region; and acquiring, for every measurement region, a tomographic image from the corrected measurement image.

According to another aspect, an optical coherence tomography apparatus divides light from a light source into measurement light and reference light and acquires a tomographic image of an object to be measured on a basis of a wavelength spectrum of coherent light of the reference light and return light, the return light returning from the object to be measured upon irradiating the measurement light onto the object to be measured. The optical coherence tomography apparatus comprises according to this aspect:

a measurement image acquisition unit to divide the object to be measured into a plurality of measurement regions adjacent to one another in a direction of irradiation of the measurement light, and to acquire a measurement image for every measurement region based on the wavelength spectrum of the coherent light;

a correction unit configured to correct, for every measurement region, a contrast of the measurement image of the measurement region; and a tomographic image acquisition unit configured to acquire, for every measurement region, a tomographic image from the corrected measurement image.

According to some aspects of the invention, there can be provided an optical coherence tomography met hod an optical coherence tomography apparatus, that can continuously join a tomographic image acquired from each of a plurality of measurement regions.

Further features of the present invention will become apparent from the following description of exemplary embodiments with reference to the attached drawings.

BRIEF DESCRIPTION OF THE DRAWINGS

FIG. 3 illustrates the widths of measurement regions.

DESCRIPTION OF THE EMBODIMENT

An optical coherence tomography apparatus according to this embodiment will be described below.

The optical coherence tomography apparatus according to the embodiment divides light from a light source into measurement light and reference light through a split optical path. The measurement light irradiates, through a measurement optical path, an object to be measured. Return light returning from the object to be measured upon irradiation of the measurement light is led through a detection optical path to a detection position. The focus position of the measurement light in the object to be measured (irradiation direction) can be controlled by a focus drive mechanism. The reference light is led through a reference optical path to a detection position. In the reference optical path, a mirror is disposed, and the position of the coherence gate can be adjusted by a mirror drive mechanism. Since the coherence gate and the focus position can be controlled in synchronization with each other, it is possible to divide the object to be measured into a plurality of measurement regions adjacent to one another along the irradiation direction and sequentially perform measurement for every region. Light led to the detection position (coherent light of the return light and the reference light) is resolved into its wavelength spectrum and is analyzed. Thus, a tomographic image of the object to be measured is acquired.

When the object to be measured is divided into a plurality of measurement regions, a situation in which the coherence gate needs to be arranged in the interior of the object to be measured occurs. Since the coherence gate refers to a position in the measurement optical path that has the same optical distance as that of the reference optical path, images that reflect each other are formed in adjacent regions across the coherence gate. The two images are equivalent, and therefore either of them may be employed for a tomographic image. Hereinafter, an image to be acquired (i.e., an image employed as the tomographic image in the region) is referred to as a "real image", and the other image is referred to as a "mirror image". In the case of adopting the SD-OCT mode, an image (measurement image) represented by coherent light includes a real image and a mirror image, and therefore separating the real image from the mirror image is indispensable.

Figure 1:
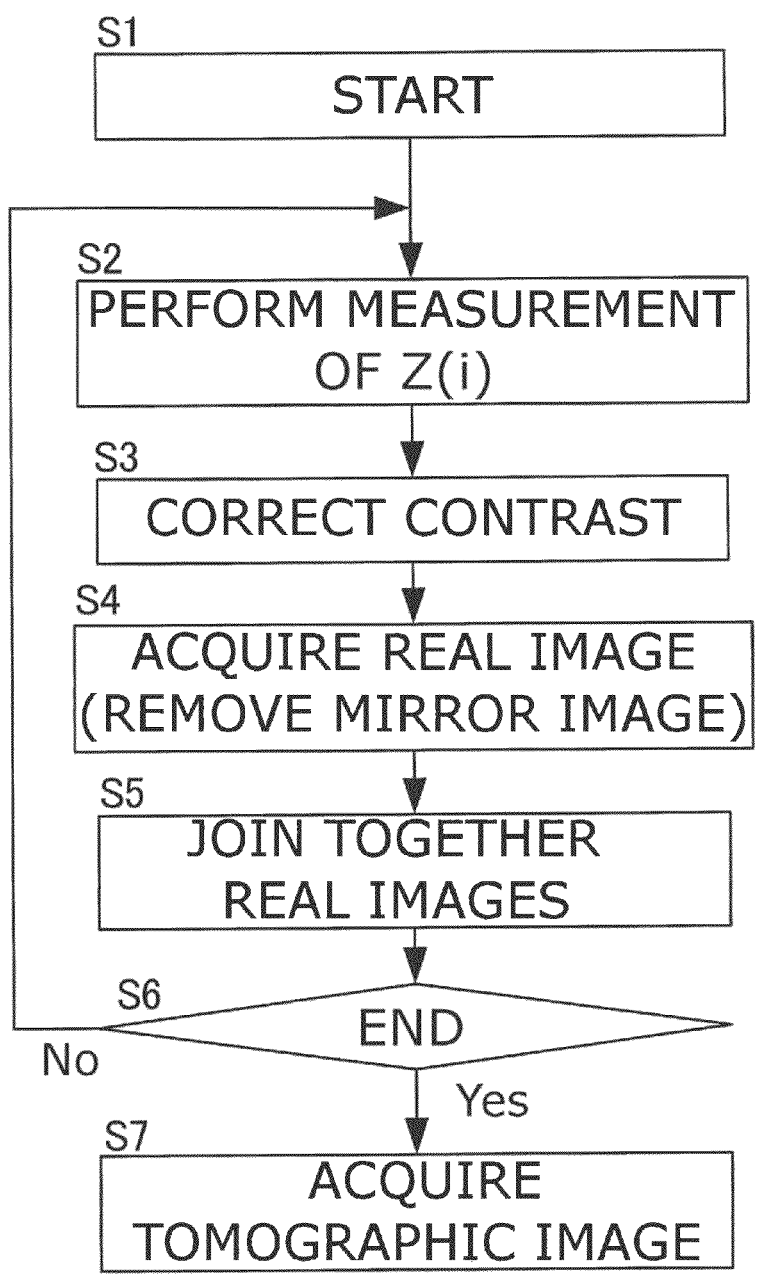
FIG. 1 is a flow chart illustrating an optical coherence tomography method according to this embodiment.

With reference to FIG. 1, an optical coherence tomography method according to this embodiment is described. In the embodiment, an object to be measured is divided into M measurement regions $Z(0)$ to $Z(M-1)$, and measurement is sequentially performed for every region.

In step S1, measurement starts.

In step S2, the coherence gate and the position of the focus are adjusted, and a measurement image of the measurement region $Z(i)$ is acquired. Note that the initial value of i is taken to be 0.

In step S3, the contrast of a measurement image of the measurement region $C(i)$ is corrected, so that the corrected measurement image (correction image) of the measurement region $Z(i)$ is acquired.

In step S4, the correction image is analyzed, and signal processing is performed to acquire a real image of the measurement region (i).

In step S5, real images from the measurement regions $Z(0)$ to $Z(i)$ are joined together.

In step S6, it is determined whether measurement has been performed for all measurement regions (whether measurement has completed for all measurement regions). If there is a measurement region for which measurement has not been performed (if $i<M-1$) (No in step S6), one is added to i, and the procedure returns to step S2. If measurement has been performed for all the measurement regions (if $i=M-1$) (Yes in step S6), the procedure proceeds to step S7. Thus, in step S7, a desired tomographic image (an image obtained by joining together real images of all the measurement regions; a tomographic image having a large measurement range of the object to be measured and a high transversal resolution) can be acquired.

Example

Next, a specific example of the optical coherence tomography apparatus according to this embodiment is described.

Specifically, an ophthalmic OCT apparatus to which this invention is applied is described below.

<Configuration of Optical Apparatus>

Figure 2:
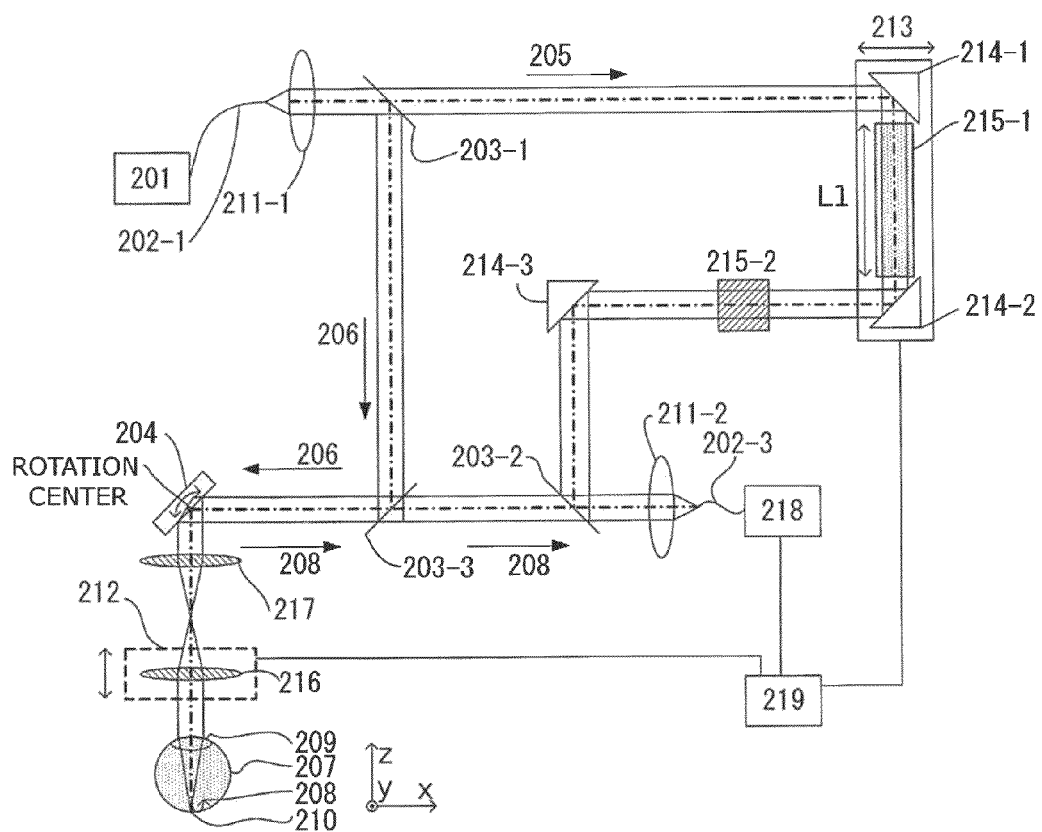
FIG. 2 illustrates a configuration of a Mach-Zehnder interference system used in an OCT apparatus according to this example.

FIG. 2 illustrates a configuration of a Mach-Zehnder interference system used in an OCT apparatus according to this example. Light emitted from a light source 201 (emitted light) passes through a single mode fiber 202-1 and is led to a lens 211-1. The emitted light is divided into reference light 205 and measurement light 206 by a beam splitter 203-1. After an eye 207, or an object to be measured, is irradiated with the measurement light 206, the measurement light 206 returns as return light 208, which is caused by reflection or scattering. The reference light 205 and the return light 208 pass through a beam splitter 203-2, a lens 211-2 and a single mode fiber 202-3 and are incident on a spectrometer 218. Data such as a wavelength spectrum of light (coherent light of the return light 208 and the reference light 205) acquired in the spectrometer is input to a computer 219. Note that the light source 201 is a super luminescent diode (SLD), which is a representative, low-coherent light source. Considering the fact that the object to be measured is an eye, it is preferable that the emitted light be infrared light (e.g., light having a center wavelength of 840 nm and a bandwidth of 50 nm).

A description is given of the reference optical path of the reference light 205. The reference light 205 resulting from division by the beam splitter 203-1 is sequentially incident on mirrors 214-1 to 214-3. The reference light 205 is led to the beam splitter 203-2 and is incident on the spectrometer 218. Note that the reference light 205 passes through the interior of a dispersion-compensating glass 215-1 between the mirrors 214-1 and 214-2. The length of the dispersion-compensating glass 215-1 is L1, which is preferably equal to twice the depth of a typical eye. This length is preferred so as to compensate the reference light 205 for dispersion caused when the measurement light 206 reflects and scatters in the eye 207. In this example, the length L1 is given to be 46 mm. This length is twice 23 mm regarded as the average diameter of an eyeball of Japanese people. Further, the mirrors 214-1 and 214-2 can be moved in directions indicated by arrows in FIG. 2 by a mirror drive mechanism 213. By moving the positions of the mirrors 214-1 and 214-2, the optical path length of the reference light 205 can be adjusted and controlled. The reference light 205 passes through the interior of a dispersion-compensating glass 215-2 between the mirrors 214-2 and 214-3. The dispersion-compensating glass 215-2 is used for dispersion compensating of an objective lens 216 and a scan lens 217 used for scanning an eye.

A description is given of the measurement optical path of the measurement light 206. The measurement light 206 resulting from division by the beam splitter 203-1 is reflected from a beam splitter 203-3 and is incident on a mirror of an XY scanner 204. The XY scanner 204 performs a raster scan of a retina 210 in a direction perpendicular to the optical axis (irradiation direction). The center of the measurement light 206 is adjusted so as to be in alignment with the center of rotation of a mirror of the XY scanner 204. The objective lens 216 and the scan lens 217 constitute an optical system for scanning the retina 210 (leading the measurement light 206 to various positions of the retina 210), and are used for scanning the retina 210 with a point in the vicinity of a cornea 209 used as a supporting point. In this example, focal distances of the objective lens 216 and the scan lens 217 are 50 mm and 50 mm, respectively. The focus position of the objective lens 216 (in the irradiation direction) can be adjusted by a focus drive mechanism 212. When the measurement light 206 is incident on the eye 207, the measurement light 206 is reflected and scattered by the retina 210, and returns as the return light 208.

The return light 208 passes through the same optical path up to the beam splitter 203-3 as the measurement light 206, and passes through the beam splitter 203-3. Then the return light 208 is led by the beam splitter 203-2 to be incident on the spectrometer 218.

Note that the focus drive mechanism 212, the mirror drive mechanism 213, the XY scanner 204 and the spectrometer 218 are controlled by the computer 219 to perform desired operation. The computer performs data processing, data saving and image processing of the spectrometer 218.

<Measurement Range>

Next, with reference to FIG. 3, the width (in the irradiation direction) of the measurement region is described. In FIG. 3, the vertical axis indicates the intensity (intensity of light; reflected intensity) and the horizontal axis indicates the position (in the light application direction) in the interior of an object to be measured. FIG. 3 schematically illustrates a case where a coherence gate 301 is placed between the measurement region Z(3) and the measurement region Z(2) adjacent thereto and measurement of measurement region Z(3) is performed. Reference numeral 302 denotes a width of each measurement region, reference numeral 303 denotes the measurement depth, and reference numeral 304 denotes the depth of focus. The measurement depth and the depth of focus will be described below.

The depth of focus (DOF) represents the visible range of an obtained image. The depth of focus is expressed by expression 1 (optical distance) using the numerical aperture (NA) of a lens used for focusing measurement light into an object to be measured and a center wavelength λ of a light source. In FIG. 3, the plus side of the range obtained by expression 1 is indicated by continuous lines and the minus side is indicated by broken lines.

$$DOF = \pm \lambda / (2NA^2) \qquad (1)$$

In cases where an object to be measured is an eye and the object to be measured is divided into six measurement regions, if the width of each measurement region 500 μm, it is preferable that the depth of focus be longer than the total length of 1000 μm (±500 μm). Note that in a typical SD-OCT apparatus, the whole length of the depth of focus is about 3 mm. As a matter of course, if the number of division increases, the measurement region can be made smaller and therefore the depth of focus can also be decreased. Note that a region exceeding the depth of focus to some extent is not without the possibility of measurement. The focus need not be set at the position of the coherence gate. However, in order to obtain a uniform image, it is preferable that the depth of focus be larger than the width of each measurement region. In the case of an OCT apparatus, the NA can be changed by changing the diameter of a light beam. In general, if the diameter of a light beam incident on an eye increases, the NA increases.

The measurement depth represents a range in which aliasing does not occur (occurrence of aliasing makes measurement difficult). The measurement depth is expressed by expression 2 (optical distance) using the number N of pixels (even number, typically the powers of 2, such as 1024 and 2048) of a line sensor of a spectrometer and a spectral bandwidth ΔK of the wave number detected by the spectrometer. In FIG. 3, the plus side and the minus side of the range obtained by expression 2 are indicated by continuous lines and broken lines, respectively.

$$L\max = \pm N/(4\Delta K) \qquad (2)$$

Assuming that the center wavelength of measurement light is 840 nm, the bandwidth is 50 nm and the number of pixels of the line sensor of the spectrometer is 1024, the range that can be measured extends up to an optical distance of about ±3.4 mm. Note that the measurement depth represented by expression 2 is a theoretical value, and in tact an actual number of sampling times is less than N because of the optical resolution of a spectrometer. The range that can be accurately replaced (measured) is therefore smaller than the theoretical measurement depth. Accordingly, the width of a measurement region needs to be set to be less than the theoretical measurement depth. In general, the relationship of the width of the measurement region<the theoretical measurement depth is satisfied. Further, in order to obtain a uniform image, it is preferable that the depth of focus (whole length) and the width of a measurement region satisfy the relationship of expression 3. That is, it is preferable that the width of the measurement region be less than one half of the depth of focus when a measurement image of the measurement region in question is acquired.

$$2 \times \text{the width of the measurement region} < \text{the depth of focus (whole length)} \quad (3)$$

In discrete Fourier transformation, each element constituting a measurement image has a discrete value which is given by expression 4 (optical distance). Here t is an integer for $0 \leq t \leq N/2$.

$$L = t/(2\Delta K) \quad (4)$$

Numerical depth resolution δ(L) is expressed by expression 5. The numerical depth resolution δ(L) is also an interval per pixel. In this example, the numerical depth resolution δ(L) is an optical distance of about 6.8 μm.

$$L\min = \delta(L) = 1/(2\Delta K) \quad (5)$$

<Method of Removing Mirror Image>

Next, with reference to FIGS. 4A to 4D, a method of acquiring a real image from a corrected measurement image (correction image) (a method of removing a mirror image) is described. In FIGS. 4A to 4D, the vertical axis indicates the intensity, and the horizontal axis indicates the position (in the irradiation direction) in the interior of an object to be measured. Note that according to a method to be described below, a mirror image in one measurement region can be removed by at least one measurement.

Figure 4A:
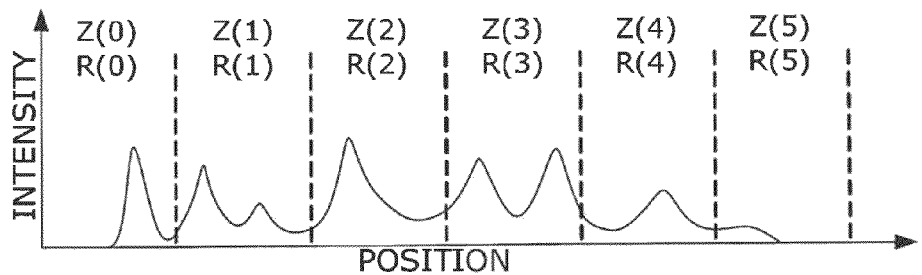
FIG. 4A illustrates an ideal tomographic image of an object to be measured.

FIG. 4A illustrates an ideal tomographic image of an object to be measured. In this example, the object to be measured is divided into measurement regions Z(0) to Z(5) at regular intervals, and measurement is performed on a region basis. Reference numerals R(0) to R(5) represent real images of the measurement regions Z(0) to Z(5), respectively. In this example, the measurement region Z(0) is disposed as a first measurement region at an end of the object to be measured. A plurality of measurement regions are set so that first to xth measurement regions (x is an integer greater than 1; the measurement regions Z(0) to Z(5) in examples of FIGS. 4A to 4D) are arranged sequentially in a direction of irradiation of measurement light. Note that with an OCT apparatus, a portion having a large difference in refractive index is measured as a large signal. Accordingly, a region at the end of the object to be measured is a region adjacent to a range in which the difference in refractive index can be ignored. Note that even in the interior of the object to be measured, if the difference in refractive index can be ignored in a range equal to or greater than the width of the measurement region, the measurement region in question and a region disposed in the outside thereof can be regarded as different objects. Therefore, such a measurement region may be regarded as a region at the end of the object to be measured.

Figure 4B:
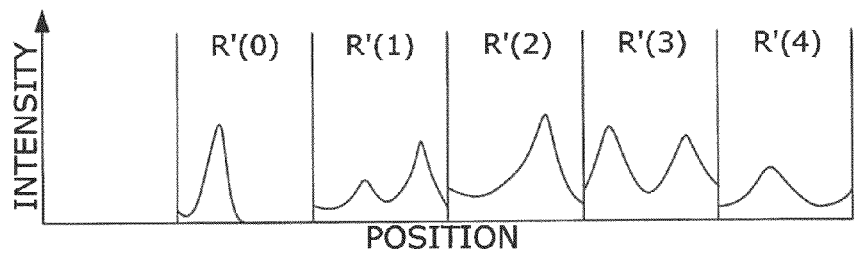
FIG. 4B illustrates mirror images reflected in measurement regions.

FIG. 4B schematically illustrates a mirror image reflected in the measurement region Z(i) (a mirror image to be superimposed on a real image of the measurement region Z(i)) when the coherence gate is placed at the boundary the measurement region Z(i−1) and the measurement region Z(i) (i>1). Since the mirror image reflected in the measurement region Z(i) is a mirror image of the real image of the measurement region Z(i−1), the mirror image is denoted by a reference character R' (i−1). Note that a measurement region of i=0 (the measurement region Z(0)) is a region at the end of the object to be measured, and therefore no mirror image appears.

Figure 4C:
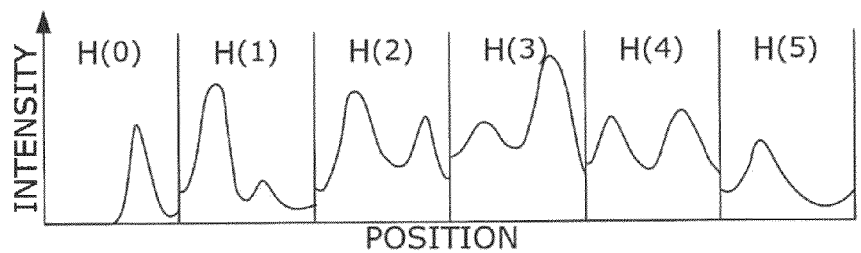
FIG. 4C illustrates a correction image of each measurement region.
Figure 7:
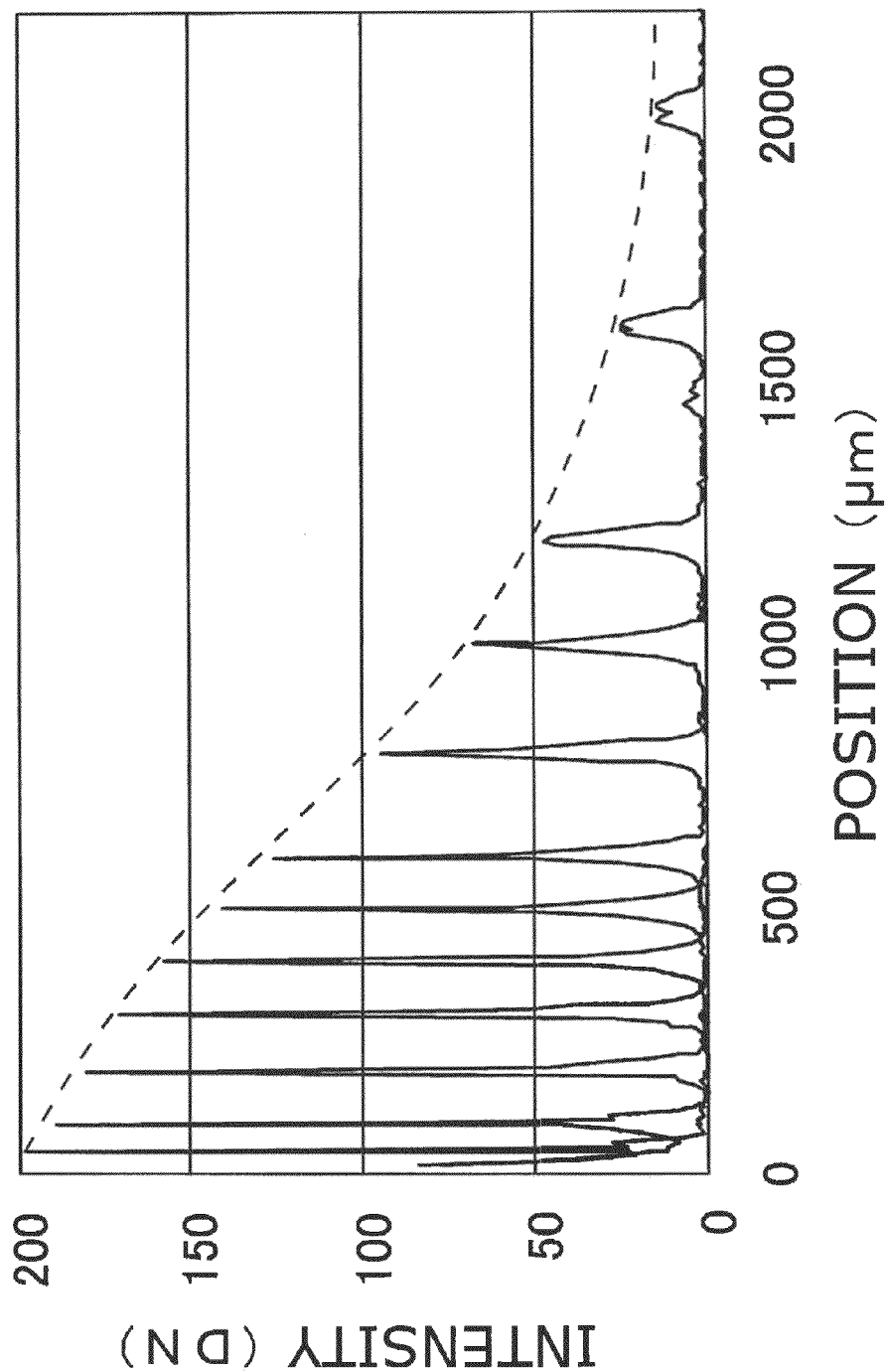
FIG. 7 illustrates a relationship of a distance between the coherence gate and a mirror and a measured intensity when the mirror is used as an object to be measured.

FIG. 4C illustrates correction images H(0) to H(3) of measurement regions when the coherence gate is placed at the boundary between the measurement region Z(i−1) and the measurement region Z(i). The correction image is obtained by dividing a measurement image S(i) by correction data D(i). The correction data is an attenuation function as illustrated in FIG. 7. The correction images of the measurement regions Z(1) to Z(5) are images in each of which a mirror image is superimposed on a real image. However, as described above, no mirror image appears in the measurement region Z(0), and therefore the correction image H(0) of the measurement region Z(0) is a real image. The correction image H(1) is expressed by expressions 6-1 and 6-2.

$$H(i) = R(i) \quad i=0 \quad (6\text{-}1)$$

$$H(i) = R(i) + R'(i-1) \quad i=1 \text{ to } 5 \quad (6\text{-}2)$$

Expression 6-1 represents that the correction image H(0) of the measurement region Z(0) is a real image R(0). Expression 6-2 represents that a real image R(i) of the measurement region Z(i) can be obtained by subtracting a mirror image R' (i−1) of a real image R(i−1) from the correction image H(i) of the measurement region Z(i).

Given that the real image obtained by removing the mirror image from the correction image is denoted by a reference character C(i), the real image C(i) is expressed by expressions 7-1 and 7-2 (reference character C' (i−1) denotes a mirror image of a zeal image C(i−1).

$$C(i) = H(i) \quad i=0 \quad (7\text{-}1)$$

$$C(i) = H(i) - C'(i-1) \quad i=1 \text{ to } 5 \quad (7\text{-}2)$$

Figure 4D:
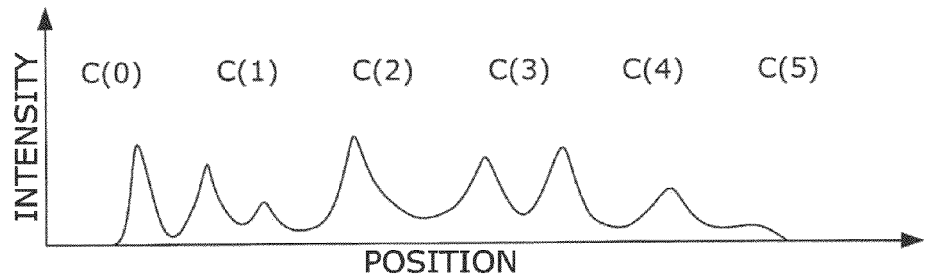
FIG. 4D illustrates a calculated real image of each measurement region.

The mirror image C' (i−1) can be calculated from the real image C(i−1). As described above, no mirror image appears in a first measurement region (the measurement region Z(0)). Therefore in this example, the correction image H(0) is employed as a tomographic image (real image) C(0) for the first measurement region. For the second to xth measurement regions in sequence, a Yth (2≤Y≤X) real image is obtained by removing a mirror image of a real image of a (Y−1)th measurement region from a correction image of a Yth measurement region. That is, in an example of FIG. 4D, the real image C(i) is calculated sequentially for i=1 to 5. This allows a real image to be acquired for every measurement region. By joining together acquired real images, a desired tomographic image can be obtained (FIG. 4D).

Note that in this example, the real image C(i) is calculated sequentially from i=1; however, the calculation method is not limited to that in this example. For example, in cases where the measurement region Z(5) is disposed at the end of the object to be measured and the coherence gate is placed at the boundary between the measurement region Z(I+1) and the measurement region Z(I) (I is not more than y and not less than 0, and y=4 in examples of FIGS. 4A to 4D), and the measurement region Z(5) may be the first measurement region. More specifically, in such a case, the correction image H(5) becomes a real image C(5), the mirror image of the real image C(I+1) of the measurement region Z(I+1) is reflected in the measurement region Z(I). Therefore, the real image C(I) can be obtained by subtracting a mirror image C' (I+1) from the correction image H(I). A real image of each measurement region can be obtained by calculating the real image C(I) sequentially for I=4 to 0.

It is conceivable that the ends are positioned in the interior of the object to be measured. For example, it is conceivable that the measurement region Z(2) and the measurement region Z(4) are regions at the ends of the object to be measured, and there is no structure in the measurement region Z(3). In this case, if the coherence gate is placed at the boundary between the measurement region (i−1) and the measurement region Z(i), the correction image H(3) becomes the mirror image of the real image C(2), and the correction image H(4) becomes the real image C(4). Therefore, in such a case, real images of the measurement regions Z(0), Z(1) and Z(5) may be calculated in the same way as described above.

Note that a method of acquiring a real image from a measurement image (a method of removing a mirror image) is not limited to the method described above. For example, as disclosed in Japanese Patent Application Laid-Open No. 11-325849, a real image of a measurement region may be acquired by performing measurement of one measurement region while changing the position of the coherence gate a plurality of times. Any method may be used if a real image of each measurement region can be acquired by it.

<Signal Processing>

Figure 5:
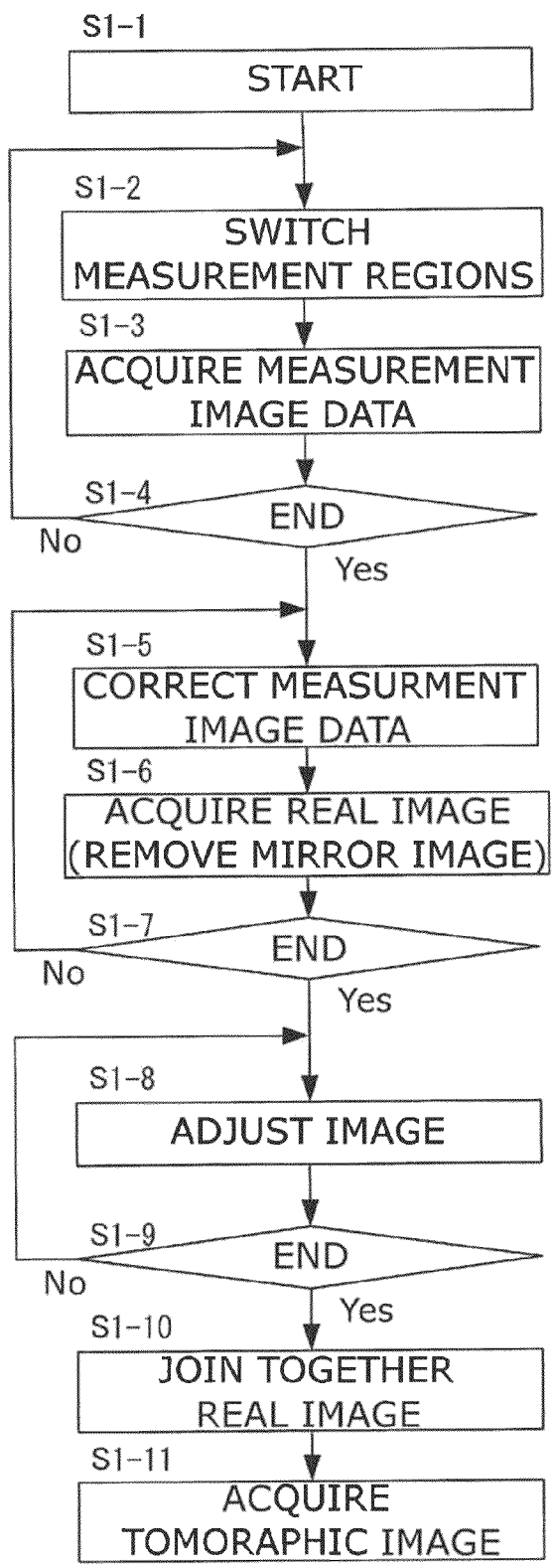
FIG. 5 is a flow chart illustrating a method of analyzing measurement image data.

With reference to FIG. 5, a method of analyzing data of measurement images (measurement image data) is described. In this example, a case in which the coherence date is placed at the boundary between the measurement region Z(i−1) and the measurement region Z(i), and measurement of the measurement region Z(i) is performed is described. Hereinafter, measurement image data of the measurement region Z(I) is denoted by reference character S(i, k), where i is a region number from 0 to M−1, and k is an element number from 0 to N−1 (both i and k are integers). M is the number of regions, and N is the number of pixels of the line sensor. Note that in this example, the element number in a measurement region ranges from 0 to n, and a measurement image is obtained in a range larger than the measurement region. Since n satisfies a relationship of n<H/2, n=500/6.8=about 74 pixels if the width of the measurement region is about 500 μm (because δ(L) =6.8 μm in this example). The width of a measurement region can be decreased by increasing the number of divisions, and therefore n is decreased with respect to the number of pixels of the line sensor. Similarly, data of the real image of each measurement region (real image data) is denoted by reference character C(i, k).

In step S1-1, measurement starts. Note that the initial value of i is taken to be 0.

In step S1-2, in order to perform measurement of the measurement region C(i), the coherence gate and the position of the focus are adjusted. Because the object to be measured is an eye, the coherence gate is placed at a position on the side of a cornea with respect to a retina. After the coherence gate is placed on the cornea side, the measurement image begins to change as the coherence gate is moved toward the retina. More specifically, the measurement image approaches closer to the coherence gate in synchronization with the movement of the coherence gate. At is position where a desired state (state where no mirror image is produced) is achieved as a result of movement, the coherence gate and the focus are stopped. This position is determined as the position of the measurement region Z(0). Note that the position of the measurement region Z(i) is a position obtained by adding the width of the measurement region×1 to the position of the measurement region Z(0). Ideally, control is performed so that the position of measurement image data S(i−1, n) is identical to the position of measurement image data S(i, 0).

In step S1-3, the measurement image data S(i, k) of the measurement region Z(i) is acquired (a measurement image acquisition unit).

In step S1-4, it is determined whether measurement has completed for desired measurement regions (up to i=5 in the examples of FIGS. 4A to 4D). If measurement has not completed (No in step S1-4), one is added to i, and the procedure returns to step S1-2. If measurement has completed (Yes in step S1-4), i returns to the initial value and the procedure proceeds to step S1-5.

In step S1-5, the contrast of measurement image data of the measurement region Z(i) is corrected (a correction unit). Correction is performed, for example, according to a correction function determined depending on an attenuation function that represents changes in intensity with respect to the position in the irradiation direction (of measurement in a measurement region. More specifically, an optical coherence tomography apparatus stores in advance or acquires the above-mentioned correction function, and performs correction for every measurement position (element position) using a value of correction function corresponding to the position (a value obtained by substituting the position for the correction function; correction data). Given that data used for correction is correction data D(i, k), the corrected measurement image data (correction image data) H(i, k) is expressed by expression 8.

$$H(i,k)=S(i,k)/D(i,k) \quad (8)$$

Note that the correction function may be a correction function itself obtained from a theory or an experiment, may also be an approximate function (a straight line or a secondary curve) of the attenuation function, and may also be a sum or a product of the attenuation function and a given coefficient. Any function may be used if it can eliminate a phenomenon (a phenomenon in which variations in contrast appear) specific to the SD-OCT.

Note that a single correction function may be used; however, if characteristics (the above-mentioned characteristics; the attenuation function) differ from one measurement region to another, correction functions are preferably prepared for every measurement region (it is preferable that the contrast of a measurement image be corrected using a correction function that differs for every measurement region). For Example, in cases where the depth of focus varies depending on the position of the focus, the characteristics vary for every measurement region, and therefore such preparation is effective.

In step S1-6, a real image of the measurement region Z(i) is calculated (a tomographic image acquisition unit).

In the measurement region Z(0), no mirror image is produced. Therefore, the relationship between the correction value data H(i, k) and the calculated real image data C(i, k) is expressed by expression 9.

$$C(i,k)=H(i,k) \quad (9)$$

Note that correction image data H(0, 0) is not tomographic data (there is no structure at the position of the element), and therefore correction value data H(0, 1) may be used in place of the correction value data H(0, 0).

If i is larger than 1, a mirror image is produced in the measurement region Z(i). Therefore, mirror image data is removed from the correction image data H(i, k) acquired in step S1-5 to acquire the real image data C(i, k). The removed mirror image data is obtained by reversing relative to the position of the coherence gate (in this example, the boundary between the measurement region and its adjacent region). More specifically, real image data C(i−1, n−k) as the mirror image data is removed from the correction image data H(i, k). Note that real image data C(i, 0) is data at the position where the coherence gate is placed, and therefore is replaced by real image data C(i−1, n) (expression 10-1). The calculated real image data C(i, k) is expressed by expression 10-2.

$$C(i,0)=C(i-1,n) \quad k=0 \tag{10-1}$$

$$C(i,k)=H(i,k)=C(i-1,n-k) \quad 0<k\le n \tag{10-2}$$

In step S1-7, it is determined whether real images of desired measurement regions (measurement regions up to i=5 in examples of FIGS. 4A to 4D) have been acquired. If the acquisition has not completed (No in step S1-7), one is added to i, and the procedure returns to step S1-5. If the acquisition has completed (Yes in step S1-7), i returns to 1 and the procedure proceeds to step S1-8.

In step S1-8, an image adjustment of the real image of Z(i) is performed. The image adjustment is adjustment of the pixel value (intensity) of a real image and the position of a measurement region (the position in the direction of irradiation of measurement light). As described above, it is desirable that the position of the real image data C(i, 0) and the position of the real image data C(i−1, n) be identical to each other. However, their positions are displaced from each other because of a position error of the coherence gate, an intensity error of a light source, and the like. In this step, such displacement is adjusted.

Figure 6:
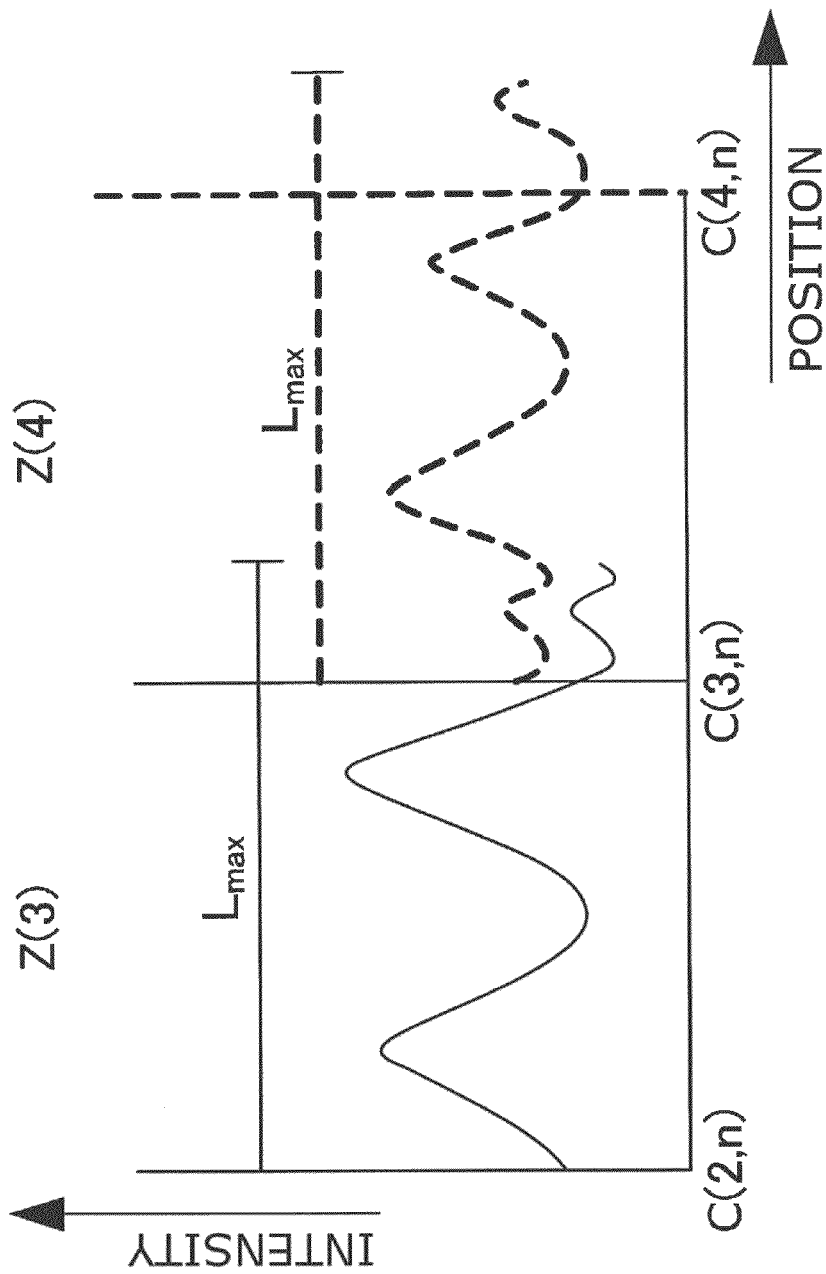
FIG. 6 illustrates a method of image adjustments of real images.

With reference to FIG. 6, the image adjustment is described. In FIG. 6, the vertical axis indicates the reflected intensity, and the horizontal axis indicates the position (in the irradiation direction) in the object to be measured. In FIG. 6, real images of the measurement regions (3) and (4) adjacent to each other are indicated by a continuous line and a broken line, respectively. A real image of the measurement region Z(i) overlaps a real image of the measurement region Z(i+1) in the range of k>n. Part or all of data of the overlapping portion is used for the image adjustment. Interpolation is performed between real image data obtained in the range of k>n, and data obtained by the interpolation may be used. Ideally, the real image data is adjusted so that the overlapping portions match each other. Note that assuming that the real image of the measurement region Z(3) has already been adjusted, adjusting the real image of the measurement region Z(4) so as to match the real image of the measurement region Z(3) is described below.

An adjustment of the positions of the measurement regions (i.e., an adjustment in the horizontal axis direction of FIG. 6) is performed so that the intensity difference of the overlapping portion of tomographic images (the continuous line and the broken line) of the measurement region and its adjacent region is equal spacing. That is, in order to cause the intensity difference of the overlapping portion of the continuous line and the broken line to be equal spacing (e.g., to minimize the dispersion of intensity differences of the overlapping portion), the broken line is shifted in the horizontal axis direction. If in the overlapping portions, there is a specific peak in each of the real images, adjustment may be performed so that their peak positions match each other. Intensity adjustment (i.e., an adjustment in the vertical axis direction of FIG. 6) is performed so that the intensity difference of the overlapping portion of tomographic images (the continuous line and the broken line) of the measurement region and its adjacent region is minimum. That is, in order to cause the intensity difference of the overlapping portion of the continuous line and the broken line to be minimum (e.g., to make the total of absolute values of intensity differences of the overlapping portion minimum), the broken line is shifted in the vertical axis direction. Note that in the image adjustment, only one of the position and the intensity of the measurement region may be adjusted. If both the position and the intensity of the measurement region are adjusted, it is preferable that the intensity be adjusted after the position is adjusted.

In step S1-9, it is determined whether the image adjustment of the real image of desired measurement regions (measurement regions up to i=5 in examples of FIGS. 4A to 4D) has completed. If the image adjustment has not been completed (No in step S1-9) one is added to i, and the procedure returns to step S1-8. If the image adjustment has completed (Yes in step S1-9, the procedure proceeds to step S1-10.

In step S1-10, real images acquired for all the measurement regions are joined together. Thus, in step S1-11, the desired tomographic image can be acquired. Note that when the real images are joined together, for the overlapping portions, their average values may be used, and an element whose number is greater than n may be ignored.

It should be noted that calculation is made with the coherence gate placed at the boundary of the measurement regions in this example; however, an error due to the spectrum of a light source is sometimes mixed to a component of S(i, k) with i in a lower order. In such a case, when a measurement image is acquired, the position of the coherence gate may be set on a side of the adjacent region with respect to the boundary between the measurement region and the adjacent region. For example, when measurement of the measurement region Z(i) is performed, the coherence gate should be shifted from the boundary between the measurement region Z(i−1) and the measurement region Z(i) toward the measurement region Z(i−1) by several to several tens of elements. The number of shifted elements may be determined depending on the coherence function of a light source, or the like.

As a result, data for every measurement region can be smoothly connected. This enables a more accurate tomographic image to be obtained.

As described above, with an optical coherence tomography apparatus according to this embodiment, the contrast of a measurement image is corrected, and a tomographic image (real image) is acquired from the corrected measurement image. Thus, the tomographic image acquired from each of a plurality of measurement regions can be continuously joined together.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-053793, filed on Mar. 6, 2009, which is hereby incorporated by reference herein in its entirety.

What is claimed is:

1. An optical coherence tomography method comprising the steps of:

acquiring, based on a wavelength spectrum of an interfering light of a return light and a reference light corresponding to a measurement light, a measurement signal at each of a plurality of measurement regions of an object adjacent to one another in a direction of irradiation of the measurement light, a position of a coherence gate and a focal position being adjusted to positions corresponding to the measurement region, the return light returning from the object irradiated by the measurement light;

acquiring an intensity change to be performed on the measurement signal at the plurality of measurement regions, the intensity change depending on the distances from the coherence gate to positions in the measurement signal; and correcting with a processor, for each measurement region, a contrast of the measurement signal using the acquired intensity change within the measurement region corresponding to the measurement signal in the direction of irradiation.

2. The method according to claim 1, further comprising acquiring, for each measurement region, a tomographic image from the corrected measurement signal, wherein the position of the measurement region in the direction of irradiation is adjusted, for every measurement region, so that a difference in intensity of an overlapping portion of a tomographic image of the measurement region and a tomographic image of a region adjacent thereto is lower than a threshold value.

3. The method according to claim 1, further comprising acquiring, for each measurement region, a tomographic image from the corrected measurement signal, wherein the intensity of the tomographic image is adjusted, for every measurement region, so that a difference in intensity of an overlapping portion of a tomographic image of the measurement region and a tomographic image of a region adjacent thereto is lower than a threshold value.

4. A non-transitory computer-readable medium that stores a program, wherein the program causes a computer to execute an optical coherence tomography method comprising the steps of:

acquiring, based on a wavelength spectrum of an interfering light of a return light and a reference light corresponding to a measurement light, a measurement signal at each of a plurality of measurement regions of an object adjacent to one another in a direction of irradiation of the measurement light, a position of a coherence gate and a focal position being adjusted to positions corresponding to the measurement region, the return light returning from the object irradiated by the measurement light;

acquiring an intensity change to be performed on the measurement signal at the plurality of measurement regions, the intensity change depending on the distances from the coherence gate to positions in the measurement signal; and correcting with a processor, for each measurement region, a contrast of the measurement signal using the acquired intensity change within the measurement region corresponding to the measurement signal in the direction of irradiation.

5. An optical coherence tomography apparatus comprising:

a computer configured to:

(a) acquire, based on a wavelength spectrum of an interfering light of a return light and a reference light corresponding to a measurement light, a measurement signal at each of a plurality of measurement regions of an object adjacent to one another in a direction of irradiation of the measurement light, a position of a coherence gate and a focal position being adjusted to positions corresponding to the measurement region, the return light returning from the object irradiated by the measurement light;

(b) acquire an intensity change to be performed on the measurement signal at the plurality of measurement regions, the intensity change depending on the distances from the coherence gate to positions in the measurement signal; and (c) correct, for each measurement region, a contrast of the measurement signal using the acquired intensity change within the measurement region corresponding to the measurement signal in the direction of irradiation.

6. The apparatus according to claim 5, wherein the computer is further configured to acquire, for each measurement region, a tomographic image from the corrected measurement signal, wherein the position of the measurement region in the direction of irradiation is adjusted, for every measurement region, so that a difference in intensity of an overlapping portion of a tomographic image of the measurement region and a tomographic image of a region adjacent thereto is lower than a threshold value.

7. The apparatus according to claim 5, wherein the computer is further configured to acquire, for each measurement region, a tomographic image from the corrected measurement signal, wherein the intensity of the tomographic image is adjusted, for every measurement region, so that a difference in intensity of an overlapping portion of a tomographic image of the measurement region and a tomographic image of a region adjacent thereto is lower than a threshold value.

8. An optical coherence tomography method that divides light from a light source into measurement light and reference light and acquires a tomographic image of an object on a basis of a wavelength spectrum of interfering light of the reference light and return light, the return light returning from the object upon applying the measurement light onto the object, the optical coherence tomography method comprising the steps of:

acquiring a measurement image at each of a plurality of measurement regions of the object adjacent to one another in a direction of irradiation of the measurement light, wherein a coherence gate is disposed at a different position for each measurement region;

acquiring an intensity change to be performed on the measurement image in each measurement region that depends on the distance from the coherence gate to a position in the measurement image;

correcting with a processor, for every measurement region, a contrast of the measurement image using the acquired intensity change within the measurement region corresponding to the measurement image in the direction of irradiation; and acquiring, for every measurement region, a tomographic image from the corrected measurement image, wherein in the step of acquiring the measurement image, for every measurement region, (a) a position of the coherence gate and a focal position are adjusted to positions corresponding to the measurement region, respectively, and (b) the measurement image is acquired based on the wavelength spectrum of the interfering light.

9. The optical coherence tomography method according to claim 8, wherein in the step of correcting the contrast of the measurement image, the contrast of the measurement image is corrected with a correction function differing for every measurement region.

10. The optical coherence tomography method according to claim 8, wherein in the step of correcting the contrast of the measurement image, the contrast of the measurement image is corrected for every measurement region according to a correction function determined based on an attenuation function representing a change in intensity with respect to a position in the measurement region in the direction of irradiation.

11. The optical coherence tomography method according to claim 8, further comprising a step of adjusting, for every measurement region, an intensity of the tomographic image and/or a position of the measurement region in the direction of irradiation.

12. The optical coherence tomography method according to claim 11, wherein the measurement image is acquired in a range larger than the measurement region, and
wherein in the step of adjusting the intensity of the tomographic image and/or the position of the measurement region in the direction of irradiation, for every measurement region, the position of the measurement region in the direction of irradiation is adjusted so that a difference in intensity of an overlapping portion of the tomographic images of the measurement region and an adjacent region thereto is equal spacing.

13. The optical coherence tomography method according to claim 11, wherein the measurement image is acquired in a range larger than the measurement region, and
wherein in the step of adjusting the intensity of the tomographic image and/or the position of the measurement region in the direction of irradiation, for every measurement region, the intensity of the tomographic image is adjusted so that a difference in intensity of an overlapping portion of the tomographic images of the measurement region and an adjacent region thereto is minimum.

14. The optical coherence tomography method according to claim 8, wherein in the step of acquiring the measurement, the position of the coherence gate is adjusted on a side of an adjacent region to the measurement region with respect to a boundary between the measurement region and the adjacent region.

15. The optical coherence tomography method according to claim 8, wherein the object is a retina.

16. The optical coherence tomography method according to claim 8, wherein, in the step of correcting the contrast of the measurement image, for every measurement region, a contrast change due to an intensity change depending on a distance from the coherence gate is corrected.

17. An optical coherence tomography apparatus that divides light from a light source into measurement light and reference light and acquires a tomographic image of an object on a basis of a wavelength spectrum of interfering light of the reference light and return light, the return light returning from the object upon irradiating the measurement light onto the object, the optical coherence tomography apparatus comprising:
a first drive mechanism that drives a device to change the position of a coherence gate;
a second drive mechanism that drives a device to change a focal position of the measurement light onto the object; and
a computer configured to:
(a) acquire a measurement image at each of a plurality of measurement regions of the object adjacent to one another in a direction of irradiation of the measurement light, wherein the coherence gate is disposed at a different position for each measurement region;
(b) acquiring an intensity change to be performed on the measurement image in each measurement region that depends on the distance from the coherence gate to a position in the measurement image;
(c) correct, for every measurement region, a contrast of the measurement image using the acquired intensity change within the measurement region corresponding to the measurement image in the direction of irradiation; and
(d) acquire, for every measurement region, a tomographic image from the corrected measurement image,
wherein in the acquiring operation the computer instructs the first and second drive mechanisms to adjust, for every measurement region, a position of the coherence gate and the focal position to positions corresponding to the measurement region, respectively, and acquires the measurement image based on the wavelength spectrum of the interfering light.

18. The optical coherence tomography apparatus according to claim 17, wherein the object is a retina.

19. The optical coherence tomography apparatus according to claim 17, wherein the correction unit corrects, for every measurement region, a contrast change due to an intensity change depending on a distance from the coherence gate.

20. An optical coherence tomography apparatus that acquires a tomographic image of an object based on interfering light resulting from interference between return light, the return light returning from the object upon irradiating measurement light onto the object, and reference light corresponding to the measurement light, the optical coherence tomography apparatus comprising:
a first drive mechanism that drives a device to change the position of a coherence gate;
a second drive mechanism that drives a device to change a focal position of the measurement light onto the object; and
a computer configured to:
(a) instruct the first driving mechanism to change the position of the coherence gate;
(b) instruct the second driving mechanism to change the focal position;
(c) acquire a first measurement image based on an interfering light at a first measurement region of the object, wherein the coherence gate is disposed at a different position for each measurement region, and to acquire a second measurement image based on an interfering light at a second measurement region adjacent to the first measurement region in a direction of irradiation of the measurement light;
(d) acquire an intensity change to be performed on the first measurement image that depends on the distance from the coherence gate to a position in the first measurement image, and acquire an intensity change to be performed on the second measurement image that depends on the distance from the coherence gate to a position in the second measurement image;
(e) correct a contrast of the first measurement image within the first measurement region using the acquired intensity change for the first measurement image and correct a contrast of the second measurement image within the second measurement region using the acquired intensity change for the second measurement image, wherein the first measurement image is acquired when the position of the coherence gate is at a first position and the focal position is at a second position, and the second measurement image is acquired when the position of the coherence gate is at a third position and the focal position is at a fourth position, wherein the third position is different from the first position, and wherein the fourth position is different from the second position.

21. The optical coherence tomography apparatus according to claim 20, wherein the object is a retina.

22. The optical coherence tomography apparatus according to claim 20, wherein the correction unit corrects, for every measurement region, a contrast change due to an intensity change depending on a distance from the coherence gate.

23. An optical coherence tomography method that acquires a tomographic image of an object based on interfering light resulting from interference between return light, the return light returning from the object upon irradiating measurement light onto the object, and reference light corresponding to the measurement light, the optical coherence tomography method comprising:

a first changing step of changing a position of a coherence gate;

a second changing step of changing a focal position;

an acquisition step of acquiring a first measurement image based on an interfering light at a first measurement region of the object, wherein the coherence gate is disposed at a different position for each measurement region, and acquiring a second measurement image based on an interfering light at a second measurement region adjacent to the first measurement region in a direction of irradiation of the measurement light;

an acquiring step of acquiring an intensity change to be performed on the first measurement image that depends on the distance from the coherence gate to a position in the first measurement image, and acquiring an intensity change on the second measurement image that depends on the distance from the coherence gate to a position in the second measurement image;

a correction step of correcting with a processor a contrast of the first measurement image within the first measurement region using the acquired intensity change for the first measurement image and correcting a contrast of the second measurement image within the second measurement region using the acquired intensity change for the second measurement image, wherein the first measurement image is acquired when the position of the coherence gate is at a first position and the focal position is at a second position, and the second measurement image is acquired when the position of the coherence gate is at a third position and the focal position is at a fourth position, wherein the third position is different from the first position, and wherein the fourth position is different from the second position.

24. The optical coherence tomography method according to claim 23, wherein the object is a retina.

25. The optical coherence tomography method according to claim 23, wherein, in the correction step, for every measurement region, a contrast change due to an intensity change depending on a distance from the coherence gate is corrected.

26. A non-transitory computer readable medium recording a computer program for causing a computer to perform an optical coherence tomography method that divides light from a light source into measurement light and reference light and acquires a tomographic image of an object on a basis of a wavelength spectrum of interfering light of the reference light and return light, the return light returning from the object upon applying the measurement light onto the object, the optical coherence tomography method comprising the steps of:

acquiring a measurement image at each of a plurality of measurement regions of the object adjacent to one another in a direction of irradiation of the measurement light, wherein a coherence gate is disposed at a different position for each measurement region;

acquiring an intensity change to be performed on the measurement image in each measurement region that depends on the distance from the coherence gate to a position in the measurement image;

correcting, for every measurement region, a contrast of the measurement image using the acquired intensity change within the measurement region corresponding to the measurement image in the direction of irradiation; and acquiring, for every measurement region, a tomographic image from the corrected measurement image, wherein in the step of acquiring the measurement image, for every measurement region, (a) a position of the coherence gate and a focal position are adjusted to positions corresponding to the measurement region, respectively, and (b) the measurement image is acquired based on the wavelength spectrum of the interfering light.

27. A non-transitory computer readable medium recording a computer program for causing a computer to perform an optical coherence tomography method that acquires a tomographic image of an object based on interfering light resulting from interference between return light, the return light returning from the object upon irradiating measurement light onto the object, and reference light corresponding to the measurement light, the optical coherence tomography method comprising:

a first changing step of changing a position of a coherence gate;

a second changing step of changing a focal position;

an acquisition step of acquiring a first measurement image based on an interfering light at a first measurement region of the object, wherein the coherence gate is disposed at a different position for each measurement region, and acquiring a second measurement image based on an interfering light at a second measurement region adjacent to the first measurement region in a direction of irradiation of the measurement light; and an acquiring step of acquiring an intensity change to be performed on the first measurement image that depends on the distance from the coherence gate to a position in the first measurement image, and acquiring an intensity change to be performed on the second measurement image that depends on the distance from the coherence gate to a position in the second measurement image;

a correction step of correcting a contrast of the first measurement image within the first measurement region using the acquired intensity change for the first measurement image and correcting a contrast of the second measurement image within the second measurement region using the acquired intensity change for the second measurement image, wherein the first measurement image is acquired when the position of the coherence gate is at a first position and the focal position is at a second position, and the second measurement image is acquired when the position of the coherence gate is at a third position and the focal position is at a fourth position, wherein the third position is different from the first position, and wherein the fourth position is different from the second position.

* * * * *